US00PP37829P2

(12) United States Plant Patent
Verhoef

(10) Patent No.: US PP37,829 P2
(45) Date of Patent: Oct. 27, 2026

(54) ***SYMPHORICARPOS* PLANT NAMED 'TW2'**

(50) Latin Name: ***Symphoricarpos doorenbosii* x *chenaultii***
Varietal Denomination: TW2

(71) Applicant: Gijsbertus Verhoef, Hazerswoude (NL)

(72) Inventor: Gijsbertus Verhoef, Hazerswoude (NL)

(73) Assignee: Bert Verhof Beheer B.V. (NL)

( * ) Notice: Subject to any disclaimer, the term of this patent is extended or adjusted under 35 U.S.C. 154(b) by 0 days.

(21) Appl. No.: 19/637,722

(22) Filed: Apr. 2, 2026

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP20,912 P2 * 3/2010 de Jong ..... A01H 6/00
Plt./226

* cited by examiner

*Primary Examiner* — Karen M Redden

(57) ABSTRACT

A new and distinct cultivar of *Symphoricarpos* plant named 'TW2' is disclosed, characterized by compact, upright plants with blue-green foliage. Plants produce abundant fruits that emerge pale whitish-green and mature to white. The new cultivar is a *Symphoricarpos*, typically produced as an outdoor ornamental plant.

3 Drawing Sheets

Latin name of the genus and species: *Symphoricarpos doorenbosii* x *chenaultii*.

Cultivar denomination: 'TW2'.

BACKGROUND OF THE INVENTION

The new cultivar is a product of a planned breeding program conducted by the inventor, to produce new *Symphoricarpos* with heavy fruiting, attractive foliage, and compact, uniform habits. The crossing resulting in the new cultivar was made in July of 2017 at a nursery in Zuid-Holland, The Netherlands.

The seed parent is the unpatented cultivar *Symphoricarpos* x *doorenbosii* 'Mother of Pearl'. The pollen parent is the unpatented *Symphoricarpos chenaultii* 'Darhalo'. The new cultivar was found and selected by the inventor in July of 2020 at the same nursery in Zuid-Holland, The Netherlands. Asexual reproduction of the new cultivar 'TW2' was first performed during May of 2021 in Zuid-Holland, The Netherlands, by softwood cuttings. Through subsequent propagation, multiple additional generations have been reproduced, having shown that the unique features of this cultivar are stable and reproduced true to type.

Date of first sale was Jun. 24, 2025, occurring in Zuid-Holland, The Netherlands. This sale was made directly by the inventor or one who obtained the claimed invention directly or indirectly from the inventor. This sale and all public disclosures made between Jun. 24, 2025 and the filing of this application fall within the exception allowed under 102(b)(1).

SUMMARY OF THE INVENTION

The cultivar 'TW2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TW2'. These characteristics in combination distinguish 'TW2' as a new and distinct *Symphoricarpos* cultivar:

1. Blue-green foliage.
2. Compact, upright plant habit.
3. Uniform branching.
4. Abundant fruits that emerge pale whitish-green and mature to white.

PARENT COMPARISONS

Plants of 'TW2' are similar to plants of the seed parent in most horticultural characteristics, however, plants of 'TW2' differ in the following:

1. Plants of the new cultivar have upright branching habits, while plants of the seed parent have arching branching habits.
2. Berry color of the new cultivar is white, while the berry color of the seed parent is light pink.

Plants of 'TW2' are similar to plants of the pollen parent in most horticultural characteristics, however, plants of 'TW2' differ in the following:

1. Plants of the new cultivar have upright, compact habits, while plants of the pollen parent have low-growing, sprawling habits.
2. Plants of the new cultivar are tightly branched, while plants of the pollen parent are loosely branched.

COMMERCIAL COMPARISON

Plants of 'TW2' can be compared to plants of the commercial cultivar *Symphoricarpos* x *doorenbosii* 'Kolmgala', U.S. Plant Pat. No. 20,912. Plants of 'TW2' are similar to plants of 'Kolmgala' in most horticultural characteristics, however, plants of 'TW2' differ in the following:

1. Plants of the new cultivar have upright branching habits, while plants of this comparator have arching branching habits.
2. Plants of the new cultivar are more tightly branched than plants of this comparator.

BRIEF DESCRIPTION OF THE PHOTOGRAPHS

The accompanying photograph in FIG. 1 illustrates in full color a typical plant of 'TW2' grown outdoor in Grand Haven, Michigan. This plant is approximately 3 years old, grown in the ground.

Figure 1:
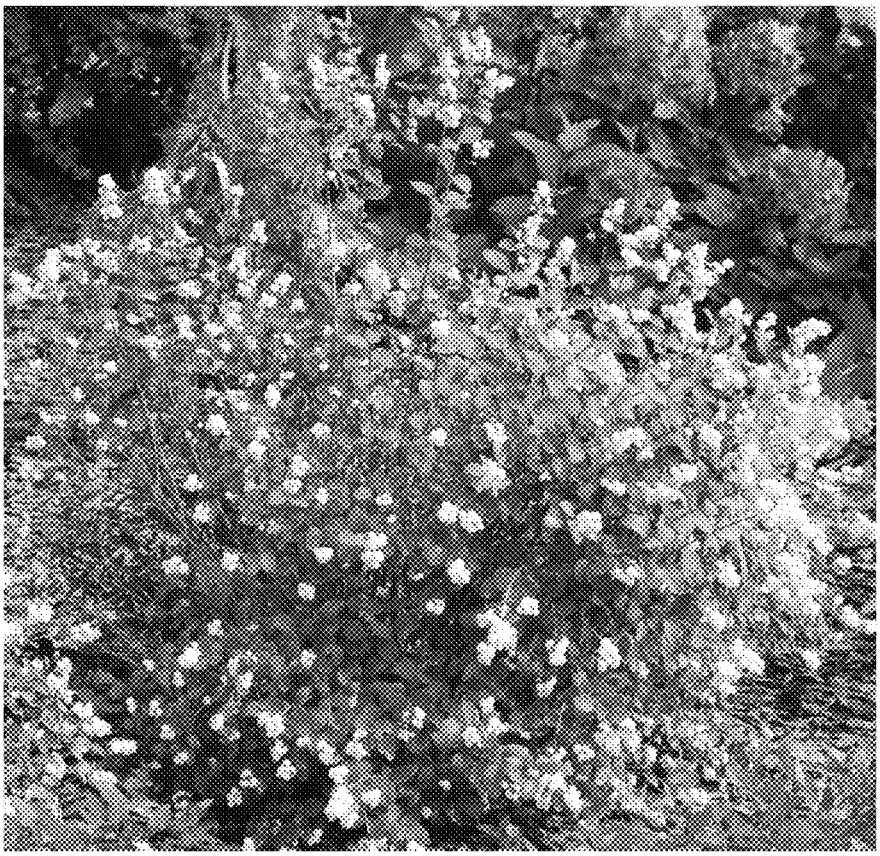
Figure 2:
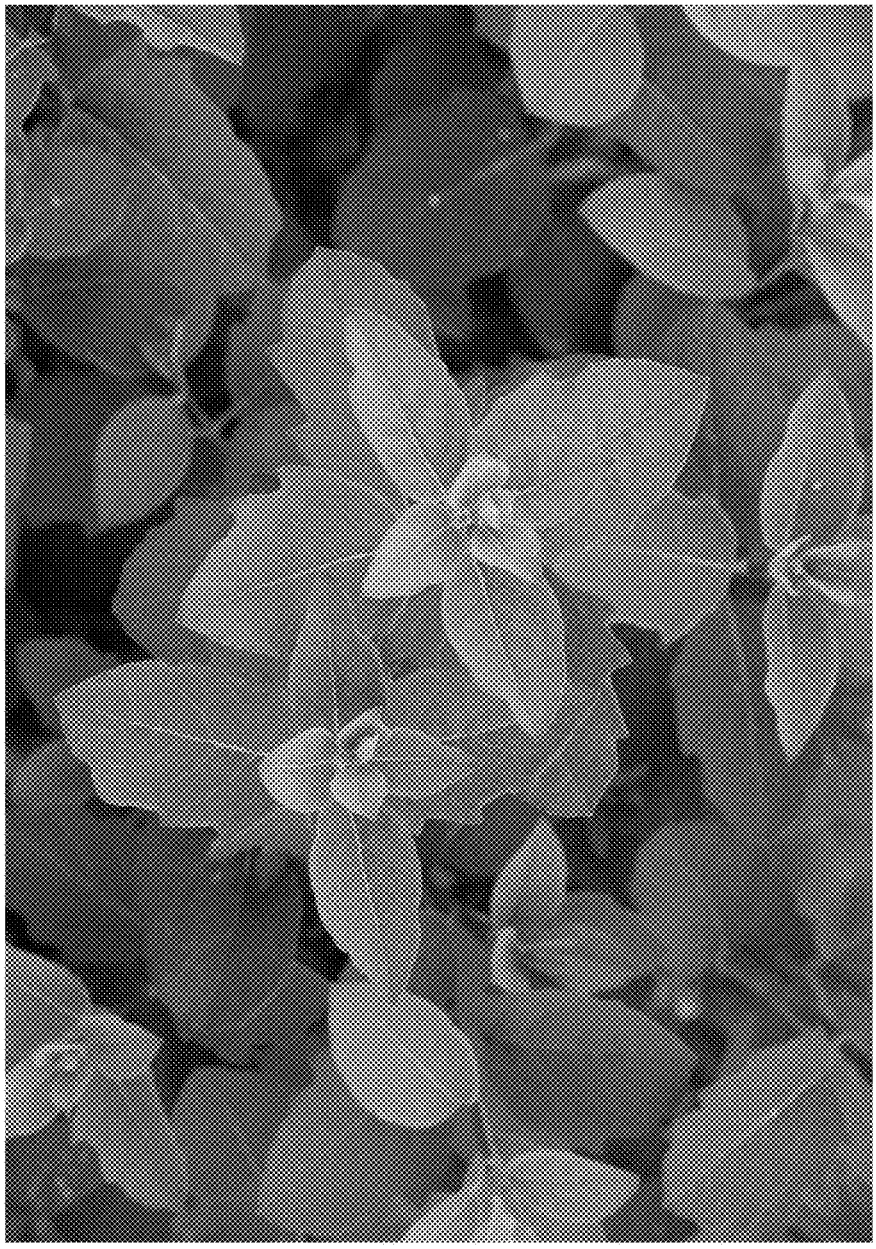
FIG. 2 illustrates in full color a close up of typical foliage of 'TW2'.
Figure 3:
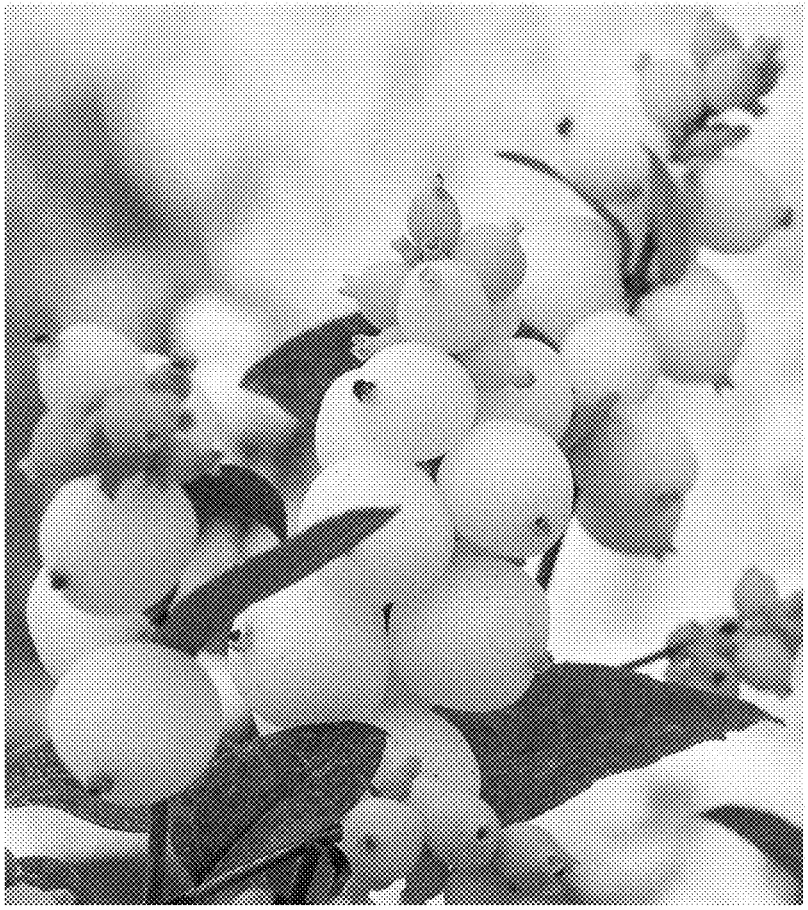
FIG. 3 illustrates in full color a close up of typical fruits of 'TW2'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'TW2' plants grown in a poly-greenhouse in Grand Haven, Michigan. The plants were 3 years old. Temperatures ranged from 5° C. to 10° C. at night to 18° C. to 27° C. during the day. No artificial light, photoperiodic treatments were given to the plants. Measurements and numerical values represent averages of typical plant types.

Botanical classification: *Symphoricarpos doorenbosii* x *chenaultii* 'TW2'.

PROPAGATION

Typical method: Softwood cuttings.
Root initiation: 6 weeks in summer.
Time to produce rooted cutting: 3 to 4 months in summer.
Roots: Medium thickness, freely branching, fibrous, moderately dense. Brown to tan in color, not accurately measured with R.H.S. chart.

PLANT

Plant type: Perennial shrub.
Growth habit: Compact, upright.
Shape: Elliptic to globose.
Height: 70 cm.
Plant spread: 65 cm.
Pot size of plant described: 3 gallon.
Age of plant described: Approximately 3 years.
Stem:
- *Branching*.—Basal, freely. Some pinching required to encourage well-rounded habit.
- *Number of lateral branches*.—About 30.
- *Shape*.—Rounded.
- *Color*.—New Growth: RHS Yellow-Green 144B with tints of Greyed-Orange 177B. Mature Growth: RHS Yellow-Green 147C. Old Growth: Near RHS Grey-Brown 199C.
- *Length*.—60 cm.
- *Width*.—4 mm.
- *Aspect*.—0° to 30° from vertical.
- *Strength*.—Moderate to high.
- *Pubescence*.—None.
- *Internode length*.—2 to 4 cm.

FOLIAGE

Leaf:
- *Arrangement*.—Opposite, single.
- *Shape*.—Elliptic.
- *Length*.—4 cm.
- *Width*.—2.75 cm.
- *Apex*.—Acute.
- *Base*.—Broadly cuneate.
- *Margin*.—Entire.
- *Texture of top surface*.—Glabrous.
- *Texture of bottom surface*.—Glabrous.
- *Pubescence*.—None.
- *Color*.—Young Foliage, Upper Side: RHS Green 138B. Thin marginal line Greyed-Red 182A on emerging foliage. Young Foliage, Under Side: RHS Yellow-Green 147B. Mature Foliage, Upper Side: Near RHS Green NN137A with a Green 133D cast. Mature Foliage, Under Side: Near RHS Green N138C.

Venation:
- *Type*.—Pinnate.
- *Color*.—Mature, Upper Side: RHS Yellow-Green 147C. Mature, Under Side: RHS Yellow-Green 147C.

Petiole:
- *Length*.—4 mm.
- *Width*.—1 mm.
- *Color*.—Upper Side: RHS Yellow-Green 146A. Under Side: RHS Yellow-Green 146A.
- *Texture*.—Upper Side: Glabrous. Under Side: Glabrous.

INFLORESCENCE

Natural flowering season: Summer (June).
Flower arrangement: Racemes at the terminal ends of lateral branches and emerging from leaf axils near the terminal ends of lateral branches.
Flowering habit: Summer-flowering, non-reblooming.
Flowers per lateral stem: 5 to 10.
Buds per lateral stem: About 30.
Flowers and buds per plant: Several hundred.
Inflorescence type: Raceme.
Inflorescence height: 1 cm.
Inflorescence width: 1.2 cm.
Fragrance: None.
Flower:
- *Shape*.—Campanulate.
- *Length*.—5 mm.
- *Diameter*.—5 mm.
- *Depth*.—5 mm.
- *Aspect*.—Outward and dropping.
- *Longevity*.—1 to 2 weeks on plant.
- *Persistence*.—Self-cleaning.

Bud:
*Length.*—2 mm.
*Diameter.*—3 mm.
*Shape.*—Globular.
*Color.*—RHS Red 39B.

Petals:
*Number.*—5.
*Appearance.*—Delicate, fused together into a bell shape.
*Arrangement.*—Stellate.
*Shape.*—Triangular.
*Tip.*—Acute.
*Base.*—Fused.
*Margin.*—Entire.
*Length.*—2 mm.
*Width.*—2 mm.
*Texture.*—Upper side: Soft, silky. Under side: Soft, silky.
*Color.*—When Opening, Upper Side: RHS Red 39C. When Opening, Under Side: RHS White N155C. Fully Opened, Upper Side: RHS Red 39C. Fully Opened, Under Side: RHS White N155C.

Sepals: Sepals are highly inconspicuous or absent.

Calyx:
*Shape.*—Cup-like.
*Length.*—1 mm.
*Diameter.*—2 mm.

Peduncle:
*Length.*—1 cm.
*Diameter.*—2 mm.
*Angle.*—0° from vertical.
*Strength.*—Moderate.
*Texture.*—Glabrous.
*Color.*—RHS Yellow-Green 144B with tints of Greyed-Orange 177B.

Pedicel:
*Length.*—1 mm.
*Diameter.*—1 mm.
*Angle.*—45° relative to peduncle.
*Texture.*—Glabrous.
*Strength.*—Moderate.
*Color.*—RHS Yellow-Green 144B.

REPRODUCTIVE ORGANS

Stamens:
*Number.*—5.
*Filament length.*—3 mm.
*Filament color.*—RHS White 155A.

Anthers:
*Shape.*—Oblong.
*Length.*—1 mm.
*Color.*—RHS Yellow 8C.
*Pollen amount.*—Moderate.
*Pollen color.*—RHS Yellow 8C.

Pistil:
*Number.*—1.
*Length.*—1.5 mm.

Stigma:
*Shape.*—Hemispherical.
*Color.*—RHS Yellow-Green 144A.
*Style length.*—1 mm.
*Style color.*—RHS Yellow-Green 144A.
*Ovary color.*—RHS Yellow-Green 144A.

SEEDS

Quantity: 2 per flower.
Shape: Ovate.
Length: 4 mm.
Diameter: 2 mm.
Color: RHS Greyed-White 156D.

FRUIT

Quantity: 80 to 100 per lateral branch; several thousand per plant.
Shape: Round.
Length: 1 cm.
Diameter: 1.2 cm.
Color:
*Immature.*—RHS Yellow-Green 145A.
*Mature.*—RHS White 155A.
Texture: Smooth-skinned; firm.
Taste: Fruit is inedible.

OTHER CHARACTERISTICS

Disease resistance: Neither resistance nor susceptibility to the normal diseases and pests of *Symphoricarpos* has been observed.
Temperature tolerance: USDA Zones 3-7.

What is claimed is:

1. A new and distinct cultivar of *Symphoricarpos* plant named 'TW2' as herein illustrated and described.

* * * * *